(12) United States Patent
Beckman et al.

(10) Patent No.: US 9,592,292 B1
(45) Date of Patent: Mar. 14, 2017

(54) SILICON NANOPARTICLE FOR PHOTODYNAMIC CANCER TREATMENT UTILIZING QUANTUM DOT OPTICAL PROPERTIES

(71) Applicants: James Beckman, Springdale, AR (US); Anatoli Ischenko, Moscow (RU)

(72) Inventors: James Beckman, Springdale, AR (US); Anatoli Ischenko, Moscow (RU)

( * ) Notice: Subject to any disclaimer, the term of this patent is extended or adjusted under 35 U.S.C. 154(b) by 0 days.

(21) Appl. No.: 15/056,446

(22) Filed: Feb. 29, 2016

Related U.S. Application Data

(63) Continuation-in-part of application No. 14/328,244, filed on Jul. 10, 2014, now abandoned, and a continuation-in-part of application No. 13/934,995, filed on Jul. 3, 2013, now abandoned, and a continuation-in-part of application No. 12/931,044, filed on Jan. 21, 2011, now abandoned, and a continuation-in-part of application No. 12/012,501, filed on Feb. 1, 2008, now abandoned.

(51) Int. Cl.
*A61K 47/00* (2006.01)
*A61K 41/00* (2006.01)
*A61K 9/51* (2006.01)
*A61N 5/06* (2006.01)

(52) U.S. Cl.
CPC ........ *A61K 41/0057* (2013.01); *A61K 9/5115* (2013.01); *A61N 5/062* (2013.01); *Y10S 977/773* (2013.01); *Y10S 977/911* (2013.01)

(58) Field of Classification Search
None
See application file for complete search history.

(56) References Cited

PUBLICATIONS

D Kovalev, M Fujii. "Silicon Nanocrystals: Photosensitizers for Oxygen Molecules." Advanced Materials, vol. 17, 2005, pp. 2531-2544.*
ML Ostraat. "Nanoparticle Nonvolatile Floating Gate Memory Devices." PhD Thesis, California Institute of Technology, 2001, pp. i-xxvii and 1-237 (264 total sheets).*

* cited by examiner

*Primary Examiner* — Isaac Shomer
(74) *Attorney, Agent, or Firm* — Keisling & Pieper PLC; David B. Pieper

(57) ABSTRACT

Quantum active sized silicon nanoparticles with a silicon core covered by a thin 0.5-1.5 nm oxide/nitride shell are described for light exposure in the 300-600 nm range for transforming atmospheric oxygen to singlet oxygen for causing cell apoptosis as a type of photodynamic cancer therapy. A method of use of the nanoparticle in a non-hydrophobic cream is also taught along with a blocking scheme for controlled reaction of the nanoparticle.

7 Claims, 2 Drawing Sheets

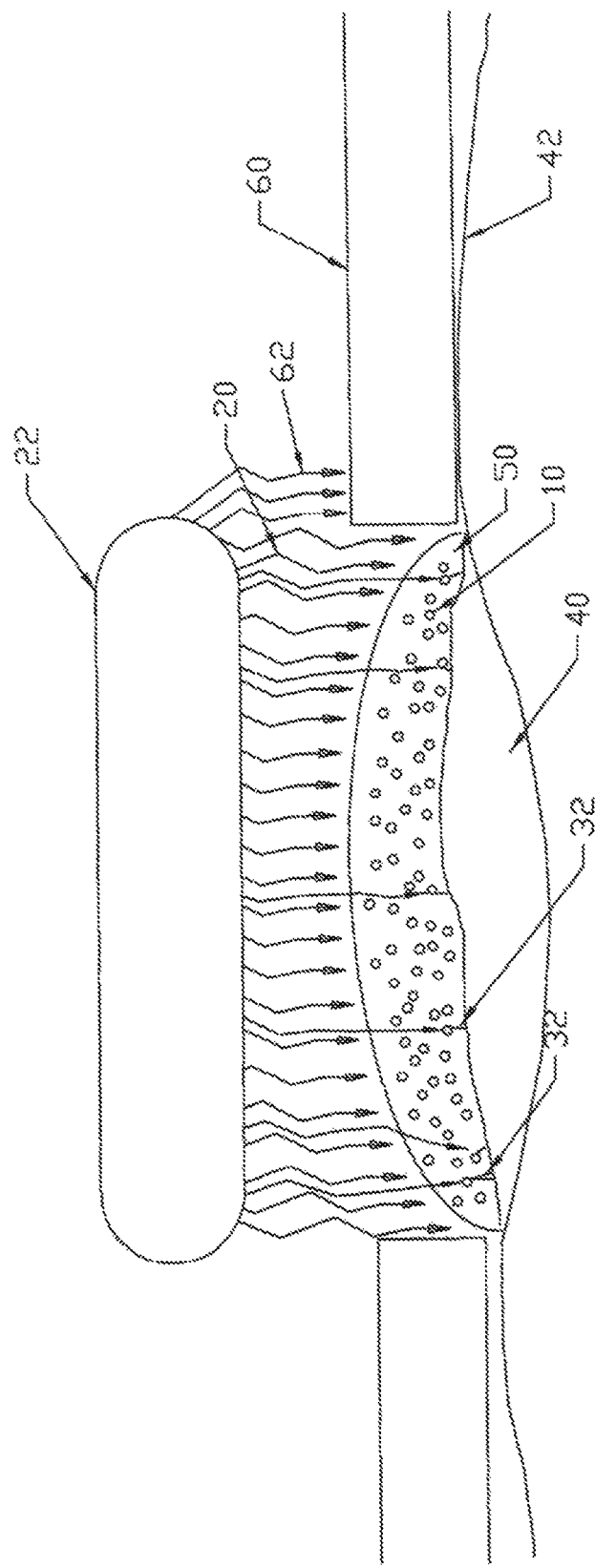

SILICON NANOPARTICLE FOR PHOTODYNAMIC CANCER TREATMENT UTILIZING QUANTUM DOT OPTICAL PROPERTIES

CROSS-REFERENCE TO RELATED APPLICATIONS

This application claims priority to and is a continuation-in-part of U.S. Utility application Ser. No. 14/328,244 filed on Jul. 10, 2014, which is a continuation-in-part of U.S. Utility application Ser. No. 13/934,995 filed on Jul. 3, 2013 by Beckman et al. entitled Silicon nanoparticle for photodynamic cancer treatment utilizing quantum dot optical properties; which is a continuation in part of U.S. Utility application Ser. No. 12/931,044 filed on Jan. 21, 2011 by Beckman et al. entitled Silicon nanoparticle for photodynamic cancer treatment utilizing quantum dot optical properties; which is a continuation in part of U.S. Utility application Ser. No. 12/012,501 filed on Feb. 1, 2008 by Beckman et al. entitled Silicon nanoparticle for photodynamic cancer treatment utilizing quantum dot optical properties; which is a continuation in part of U.S. provisional application Ser. No. 60/898,956 filed on Feb. 1, 2007 by Beckman et al. entitled Nanoparticle skin cancer treatment. Each of these prior applications is incorporated by reference in their entirety.

STATEMENT REGARDING FEDERALLY SPONSORED RESEARCH OR DEVELOPMENT

Not Applicable.

REFERENCE TO A MICROFICHE APPENDIX

Not Applicable.

RESERVATION OF RIGHTS

A portion of the disclosure of this patent document contains material which is subject to intellectual property rights such as but not limited to copyright, trademark, and/or trade dress protection. The owner has no objection to the facsimile reproduction by anyone of the patent document or the patent disclosure as it appears in the Patent and Trademark Office patent files or records but otherwise reserves all rights whatsoever.

BACKGROUND OF THE INVENTION

1. Field of the Invention

The present invention relates to improvements in the use of quantum dot energy as photosensibilizers to create singlet oxygen from inert nanoparticles. More particularly, the invention relates to improvements particularly suited for effecting cell apoptosis causing natural cell death by generating singlet oxygen from inert nanoparticles having a silicon core with a thin oxygen and/or nitrogen shell capable of being activated to stimulate formation of said singlet oxygen radicals with a normal low cost visible light source generator. In particular, the present invention relates specifically to a silicon nanoparticle with a 0.5 to 1.5 nm shell.

2. Description of the Known Art

As will be appreciated by those skilled in the art, various types of quantum dots are known in various forms. Similarly, various photodynamic cancer treatments are known than use photo sensibilizers. What is not know is the use of an inert quantum dot capable of use with low power common light sources for inexpensive cancer therapy. Patents applications disclosing information relevant to quantum dots include U.S. provisional application Ser. No. 60/730,271 filed on Oct. 26, 2005; U.S. application Ser. No. 11/094,837 filed on Mar. 30, 2005; and U.S. provisional application Ser. No. 60/558,209 filed on Mar. 30, 2004. Each of these applications is hereby expressly incorporated by reference in their entirety.

As will be appreciated by those skilled in the art, silicon nanoparticles are known in various forms. Patents disclosing information relevant to silicon nanoparticles include U.S. Pat. No. 7,078,276, issued to Zurcher, et al. on Jul. 18, 2006; U.S. Pat. No. 7,020,372, issued to Lee, et al. on Mar. 28, 2006; U.S. Pat. No. 7,005,669, issued to Lee on Feb. 28, 2006; U.S. Pat. No. 6,961,499, issued to Lee, et al. on Nov. 1, 2005; U.S. Pat. No. 6,846,565, issued to Korgel, et al. on Jan. 25, 2005; and U.S. Pat. No. 6,268,041, issued to Goldstein on Jul. 31, 2001; U.S. Pat. No. 6,992,298, issued to Nayfeh, et al. on Jan. 31, 2006. Each of these patents is hereby expressly incorporated by reference in their entirety.

Other publications to consider include: 1. C. Delerue, G. Allan, M. Lannoo, Optical band gap of Si nanoclusters, J. Lumin. 1999, v. 80, pp. 65-73; 2. Y. D. Glinka, Size effect in self-trapped exciton photoluminescence from SiO2-based nanoscale materials, Physical Review B., 2001, v. 64, p 085421; 3. S. Altman, D. Lee, J. D. Chung, J. Song, M. Choi, Light absorption of silica nanoparticles, Phys. Rev. B., 2001, v. 63, p. 161402; 4. L. Brus, Electronic Wave Functions in Semiconductor Clusters: Experiment and Theory, J. Phys. Chem., 1986, v. 90, pp. 2555-2560; 5. E. A. Konstantinova, V. A. Demin, A. S. Vorontsov, Yu. V. Ryabchikov, I. A. Belogorokhov, L. A. Osminkina, P. A. Forsh, P. K. Kashkarov, V. Yu. Timoshenko, Electron Paramagnetic Resonance and Photoluminescence Study of Si Nanocrystals-Photosensitizers of Singlet Oxygen Molecules, J. Non-Cryst. Sol., 2006, v. 352, pp. 1156-1159; 6. N. J. Turro, Modern Molecular Photochemistry, University Science Publications, Sausalito, Calif., 1991; 7. Kuz'min G. P., Karasev M. E., Khokhlov E. M., Kononov N. N., Korovin S. B., Plotnichenko V. G., Polyakov S. N., V. I. P., O. V. T. Nanosize Silicon Powders: The Structure and Optical Properties//Laser Phys.—2000.—V. 10.—No. 4.—P. 939-945; 8. A. A. Ischenko, A. A. Sviridova, K. V. Zaitseva, O. A. Rybaltovsky, V. N. Bagratashvili, A. I. Belogorokhov, V. V. Koltashev, V. G. Plotnichenko, I. A. Tutorsky, Spectral properties of siliceous nanocomposite materials. Proc. SPIE, 2006, v. 6164, pp. 616406-1-616406-7; 9. A. O. Rybaltovsky, V. A, Radzig, A. A. Sviridova, A. A. Ischenko, Effect of annealing on the Silicon Nanocrystals optical properties, Nanotechnic, 2007, v.13(11), pp.116-121; and 10. W. Kueng, E. Silber, and U. Eppenberger, Annals of Biochemistry, 1989, v.182, pp.16-21. Each of these patents and/or publications is hereby expressly incorporated by reference in their entirety. As noted by these disclosures, the prior art is very limited in its teaching and utilization, and an improved nanocrystaline based therapy is needed to overcome these limitations.

The present invention is addressed to a previously undiscovered method for generating singlet oxygen for use in photodynamic therapy. Several issues need to be considered to understand the background of the present invention, including photodynamic therapy, singlet oxygen, excitons, and limitations of the prior art teachings.

Chemical Based Photodynamic Therapy

The following basic background information provided in paragraphs (a) through (e) was presented by the U.S.

National cancer institute in describing the old methods for Photodynamic therapy (PDT):

(a) PDT is a treatment that uses a drug (chemical), called a photosensitizer or photosensitizing agent, and a particular type of light. When photosensitizers are exposed to a specific wavelength of light, they produce an activated form of oxygen that kills nearby cells. Each photosensitizer is activated by light of a specific wavelength. This wavelength determines how far the light can travel into the body. Thus, doctors use specific photosensitizers and wavelengths of light to treat different areas of the body with PDT. In the first step of PDT for cancer treatment, a photosensitizing agent is injected into the bloodstream. The agent is absorbed by cells all over the body, but stays in cancer cells longer than it does in normal cells. Approximately 24 to 72 hours after injection, when most of the agent has left normal cells but remains in cancer cells, the tumor is exposed to light. The photosensitizer chemical in the tumor absorbs the light and produces an active form of oxygen that destroys nearby cancer cells by killing them (necrosis) rather than by the natural cell death mechanism (apoptosis). In addition to directly killing cancer cells, PDT appears to shrink or destroy tumors in two other ways. The photosensitizer can damage blood vessels in the tumor, thereby preventing the cancer from receiving necessary nutrients. In addition, PDT may activate the immune system to attack the tumor cells.

(b) The light used for PDT can come from a laser or other sources of light. Laser light can be directed through fiber optic cables (thin fibers that transmit light) to deliver light to areas inside the body. For example, fiber optic cable can be inserted through an endoscope (a thin, lighted tube used to look at tissues inside the body) into the lungs or esophagus to treat cancer in these organs. Other light sources include light-emitting diodes (LEDs), which may be used for surface tumors, such as skin cancer. PDT is usually performed as an outpatient procedure. PDT may also be repeated and may be used with other therapies, such as surgery, radiation, or chemotherapy.

(c) To date, the U.S. Food and Drug Administration (FDA) has approved the photosensitizing agent called porfimer sodium, or PHOTOFRIN®, for use in PDT to treat or relieve the symptoms of esophageal cancer and non-small cell lung cancer. Porfimer sodium is approved to relieve symptoms of esophageal cancer when the cancer obstructs the esophagus or when the cancer cannot be satisfactorily treated with laser therapy alone. Porfimer sodium is used to treat non-small cell lung cancer in patients for whom the usual treatments are not appropriate, and to relieve symptoms in patients with non-small cell lung cancer that obstructs the airways. In 2003, the FDA approved porfimer sodium for the treatment of precancerous lesions in patients with Barrett's esophagus (a condition that can lead to esophageal cancer). Porfimer sodium makes the skin and eyes sensitive to light for approximately 6 weeks after treatment. Thus, patients are advised to avoid direct sunlight and bright indoor light for at least 6 weeks. Photosensitizers tend to build up in tumors and the activating light is focused on the tumor. As a result, damage to healthy tissue is minimal. However, PDT can cause burns, swelling, pain, and scarring in nearby healthy tissue. Other side effects of PDT are related to the area that is treated. They can include coughing, trouble swallowing, stomach pain, painful breathing, or shortness of breath; these side effects are usually temporary.

(d) The light needed to activate most photosensitizers cannot pass through more than about one-third of an inch of tissue (1 centimeter). For this reason, PDT is usually used to treat tumors on or just under the skin or on the lining of internal organs or cavities. PDT is also less effective in treating large tumors, because the light cannot pass far into these tumors. PDT is a local treatment and generally cannot be used to treat cancer that has spread (metastasized).

(e) Researchers continue to study ways to improve the effectiveness of PDT and expand it to other cancers. Clinical trials (research studies) are under way to evaluate the use of PDT for cancers of the brain, skin, prostate, cervix, and peritoneal cavity (the space in the abdomen that contains the intestines, stomachs and liver). Other research is focused on the development of photosensitizers that are more powerful, more specifically target cancer cells, and are activated by light that can penetrate tissue and treat deep or large tumors. Researchers are also investigating ways to improve equipment and the delivery of the activating light.

As noted by this basic information, several problems exist with current photosensibilizers due to patient sensitivity increases for up to 6 week periods, overexposure of the patient to the photosensibilizers, the expense and difficulty associated with this class of photosensibilizers, and most importantly the difficulty of precise delivery of the singlet oxygen to specific tumor cells by having to "shoot beams of light" onto targets of photosensitizing agents administered by system injection to all body cells. Thus, an improved photosensibilizer for the generation of a singlet oxygen is needed along with an improved and precise method of application and treatment delivery.

Apoptosis

Apoptosis (pronounced ă-pŏp-tō'sĭs[1]) is a form of programmed cell death in multicellular organisms. It is the primary method of programmed cell death (PCD) that allows body organs to remain of similar size throughout adult life even as cells replace themselves continually in the normal life process. It involves a series of biochemical events leading to a characteristic cell morphology and death, in more specific terms, a series of biochemical events that lead to a variety of morphological changes, including blebbing, changes to the cell membrane such as loss of membrane asymmetry and attachment, cell shrinkage, nuclear fragmentation, chromatin condensation, and chromosomal DNA fragmentation. Processes of disposal of cellular debris whose results do not damage the organism differentiates apoptosis from necrosis.

In contrast to necrosis, which is a form of traumatic cell death that results from acute cellular injury, apoptosis, in general, confers advantages during an organism's life cycle. Between 50 billion and 70 billion cells die each day due to apoptosis in the average human adult. For an average child between the ages of 8 and 14, approximately 20 billion to 30 billion cells die a day. In a year, this amounts to the proliferation and subsequent destruction of a mass of cells equal to an individual's body weight.

Research on apoptosis has increased substantially since the early 1990s. In addition to its importance as a biological phenomenon, defective apoptotic processes have been implicated in an extensive variety of diseases. Excessive apoptosis causes hypotrophy, such as in ischemic damage, whereas an insufficient amount results in uncontrolled cell proliferation, such as cancer.

Apoptosis can occur when a cell is damaged beyond repair, infected with a virus, or undergoing stress conditions such as starvation. DNA damage from ionizing radiation or toxic chemicals can also induce apoptosis via the actions of the tumour-suppressing gene. The "decision" for apoptosis can come from the cell itself, from the surrounding tissue, or from a cell that is part of the immune system. In these cases apoptosis functions to remove the damaged cell, preventing it from sapping further nutrients from the organism, or to prevent the spread of viral infection.

The process of apoptosis is controlled by a diverse range of cell signals, which may originate either extracellularly (extrinsic inducers) or intracellularly (intrinsic inducers). Extracellular signals may include hormones, growth factors, nitric oxide or cytokines, and therefore must either cross the plasma membrane or transduce to effect a response. These signals may positively or negatively induce apoptosis; in this context the binding and subsequent initiation of apoptosis by a molecule is termed positive, whereas the active repression of apoptosis by a molecule is termed negative.

Dying cells that undergo the final stages of apoptosis display phagocytotic molecules, such as phosphatidylserine, on their cell surface. Phosphatidylserine is normally found on the cytosolic surface of the plasma membrane, but is redistributed during apoptosis to the extracellular surface by a hypothetical protein known as scramblase. These molecules mark the cell for phagocytosis by cells possessing the appropriate receptors, such as macrophages. Upon recognition, the phagocyte reorganizes its cytoskeleton for engulfment of the cell. The removal of dying cells by phagocytes occurs in an orderly manner without eliciting an inflammatory response.

Singlet Oxygen

Singlet oxygen is the common name used for the two metastable states of molecular oxygen (O2) with higher energy than the ground state triplet oxygen. The energy difference between the lowest energy of O2 in the singlet state and the lowest energy in the triplet state is about 3625 kelvin ($Te(a^1\Delta g \leftarrow X^3\Sigma g-)=7918.1$ cm−1.) Molecular oxygen differs from most molecules in having an open-shell triplet ground state, $O2(X^3\Sigma g-)$. Molecular orbital theory predicts two low-lying excited singlet states $O2(a^1\Delta g)$ and $O2(b^1\Sigma g+)$. These electronic states differ only in the spin and the occupancy of oxygen's two degenerate antibonding πg-orbitals. The $O2(b^1\Sigma g+)$-state is very short lived and relaxes quickly to the lowest lying excited state, $O2(a^1\Delta g)$. Thus, the $O2(a^1\Delta g)$-state is commonly referred to as singlet oxygen.

The energy difference between ground state and singlet oxygen is 94.2 kJ/mol and corresponds to a transition in the near-infrared at ~1270 nm. In the isolated molecule, the transition is strictly forbidden by spin, symmetry and parity selection rules, making it one of nature's most forbidden transitions. In other words, direct excitation of ground state oxygen by light to form singlet oxygen is very improbable. As a consequence, singlet oxygen in the gas phase is extremely long lived (72 minutes). Interaction with solvents, however, reduces the lifetime to microsecond or even nanoseconds.

Formation of Singlet Oxygen

Formation of singlet oxygen is known using chemical reactions or the use light on dyes as shown in (WO/1997/029044) DEVICE FOR PRODUCING A SINGLET OXYGEN ACTIVATED GAS STREAM, August, 1997 which notes the following: Known equipment exists for the production of singlet oxygen and photo-sensitive means for this purpose. In "Singlet O2" by Aryeh A. Frimer, CRC Press Inc., USA 1985, the principles are described for production of singlet oxygen in a gaseous state, and thereby activated gas. WO patent application 9007144 indicates various photo-sensitive means for, in combination with light radiation, forming singlet oxygen which is employed for oxidation of specific compounds. WO patent application 9100241 concerns decomposition of nitrogen oxides. The decomposition is performed by the influence of light on a catalyst when a radiation source is placed against a transparent wall of a container. DE patent 4125254 describes a device for producing activated oxygen. The device which is described consists of a chamber in which through-flowing oxygen is irradiated from a UV radiation source and the chamber is divided by partitions into forward and backward flow paths, thus obtaining the longest possible flow path in order to achieve the longest possible treatment time for the oxygen. There is further described a finishing treatment with magnetic influence of the end product. However, the device is not intended for generating singlet oxygen, but for so-called "softer activation of the oxygen". DE patent 3606925 describes a device for producing singlet oxygen and possibly ozone. The device is tubular, with a lamp in the middle and with a through-flow of oxygen, where a layer of metal oxides or a fluoridating material is provided on the surfaces of the device. The design of the device is extremely complicated. The known devices which have been employed for production of singlet oxygen have been large and cumbersome and/or complicated or it has not been possible to document that the production of singlet oxygen has actually taken place.

Sensibilizer

It is known that electrons are liberated when electromagnetic radiation, such as sun light, impinges on substances having a low ionization potential, so-called sensibilizers, whereby an electron-ion pair is formed.

Exciton

An exciton is a bound state of an electron and an imaginary particle called an electron hole in an insulator or semiconductor, and such is a Coulomb-correlated electron-hole pair. It is an elementary excitation, or a quasiparticle of a solid.

A vivid picture of exciton formation is as follows: a photon (particle of light energy) enters a semiconductor, exciting an electron from the valence band into the conduction band. The missing electron in the valence band leaves a hole behind, of opposite electric charge, to which it is attracted by the Coulomb force. The exciton results from the binding of the electron with its hole; as a result, the exciton has slightly less energy than the unbound electron and hole. The wave function of the bound state is hydrogenic (an "exotic atom" state akin to that of a hydrogen atom). However, the binding energy is much smaller and the size much bigger than a hydrogen atom because of the effects of screening and the effective mass of the constituents in the material.

Silicon Based Nanocrystals

A nanocrystal is a crystalline material with dimensions measured in nanometers; a nanoparticle with a structure that is mostly crystalline. These materials are of huge technological interest since many of their electrical, opto-electrical, and thermodynamic properties show strong size dependence and can therefore be controlled through careful manufacturing processes. Nanocrystal is part of the large "family" of nanotechnology. Semiconductor nanocrystals in the sub-10 nm size range are often referred to as nanoparticles.

Nanoparticles

A nanoparticle is defined by size alone. A nanostructure semiconductor is composed such that it confines the motion of conduction band electrons, valence band holes, or excitons (bound pairs of conduction band electrons and valence band holes) in all three spatial directions. The confinement can be due to electrostatic potentials (generated by external electrodes, doping, strain, impurities), the presence of an interface between different semiconductor materials (e.g. in core-shell nanocrystal systems), the presence of the semiconductor surface (e.g. semiconductor nanocrystal), or a combination of these. A quantum dot is a quantity of light/wave energy that has a discrete quantized amount of energy specific to the light spectrum. The corresponding wave functions are spatially localized within the particle, but extend over many periods of the crystal lattice. A quantum active nanoparticle contains a small finite number (of the order of 1-100) of conduction band electrons, valence band holes, or excitons, i.e., a finite number of elementary electric charges.

Small quantum active particles, such as colloidal semiconductor nanocrystals, can be as small as 2 to 10 nanometers, corresponding to 10 to 50 atoms in diameter and a total of 100 to 100,000 atoms within the quantum active particle volume. Self-assembled quantum nanoparticles are typically between 10 and 50 nm in size. Nanoparticles defined by lithographically patterned gate electrodes, or by etching on two-dimensional electron gases in semiconductor heterostructures can have lateral dimensions exceeding 100 nm. At 10 nm in diameter, nearly 3 million nanoparticles could be lined up end to end and fit within the width of a human thumb (note: they cannot be used when lined up like this at the present).

The ability to tune the size of nanoparticles is advantageous for many applications. For instance, larger quantum active nanoparticles have spectra shifted towards the red compared to smaller dots, and exhibit less pronounced quantum properties. Conversely the smaller particles allow one to take advantage of quantum properties.

In large numbers, nanoparticles may be synthesized by means of a colloidal synthesis. Colloidal synthesis is by far the cheapest and has the advantage of being able to occur at benchtop conditions. It is acknowledged to be the least toxic of all the different forms of synthesis.

Nanoparticles may have the potential to increase the efficiency and reduce the cost of today's typical silicon photovoltaic cells. According to experimental proof from 2006, nanoparticles of lead selenide can produce as many as seven excitons from one high energy photon of sunlight (7.8 times the bandgap energy). Quantum dot nanoparticle photovoltaics would theoretically be cheaper to manufacture, as they can be made "using simple chemical reactions".

Mercury Vapor Lamps

A mercury-vapor lamp is a gas discharge lamp which uses mercury in an excited state to produce light. The arc discharge is generally confined to a small fused quartz arc tube mounted within a larger borosilicate glass bulb. The outer bulb may be clear or coated with a phosphor; in either case, the outer bulb provides thermal insulation, protection from ultraviolet radiation, and a convenient mounting for the fused quartz arc tube. Mercury vapor lamps (and their relatives) are often used because they are relatively efficient. Phosphor coated bulbs offer better color rendition than either high- or low-pressure sodium vapor lamps. They also offer a very long lifetime, as well as intense lighting for several applications. A closely-related lamp design called the metal halide lamp uses various other elements in an amalgam with the mercury. Sodium iodide and Scandium iodide are commonly in use. These lamps can produce much better quality light without resorting to phosphors.

With all of this information in mind, it may be seen that these prior art teachings, publications, and patents are very limited in their teaching and utilization, and an improved silicon nanoparticle and method of use is needed to overcome these limitations.

SUMMARY OF THE INVENTION

The present invention is directed to an improved nanoparticle based photodynamic cancer treatment. In accordance with one exemplary embodiment of the present invention, a silicon nanoparticle with a precisely controlled thin nitride and/or oxide shell is provided for use as a sensibilizer for converting room and/or supplied oxygen at room temperature and pressure to singlet oxygen for imparting energy directly to adjacent cancer cells to induce apoptosis. Major advantages of this system include the inert nature of the nitride/oxide shell silicon nanoparticle, the ability to specifically target the cancerous area without exposing the entire body to the treating agents, and the non-inflammatory method of cancer death and natural body disposal, the comparatively low cost of the nanocrystal and the generating light source, and the ease of protecting other areas from the light source and the singlet oxygen generated, among other advantages.

In one embodiment of the present invention, a method is taught for topical cancer treatment. A topical application of a non-lipophobic medium (paste, gel, or solution) containing the nitride/oxide shell silicon nanoparticle is placed on the surface of skin cancer cells in a free oxygen environment. Subsequent exposure of the invention (in its medium) paste covering the cancer cells with a laser or light beam in the visible spectrum of 320-650 nanometer wavelength can be directed at/to the new silicon nanoparticle paste on the skin cancer. The light energy will be temporarily trapped within the nanoparticle itself. By controlling the size or diameter of our silicon kernels and by modification of the silicon oxide coating thickness of the particle, the light energy "trapped" within the silicon nanoparticle then becomes useful as an "internal reactor" device for exiton creation which then reacts its energy "through" the oxide/nitride shell to oxygen on the outer surface. The energy inside the silicon particles has a direct effect on oxygen in the room atmosphere in attracting the oxygen molecules to the surface of the nanoparticle. The energy then acts via the oxide coating of the kernel to cause the production and the release of extremely powerful free radicals, singlet oxygen or peroxides on the outer adjacent nanoparticle surface. These free radicals, formed in a medium of the nanoparticles carefully applied to cultures of skin cancer cells, have been shown in skin cell melanoma cultures to kill 90% of the cancer cells in a one hour exposure time to the halogen light source.

The present invention is directed to the invention of the shell thickness in a manner to be responsive to the exciton formation inside the core and converting this energy into singlet oxygen external to the core; creating the new/altered nitride and oxide coating on the nanoparticle; the method of using a directed light source and its "trapped light energy" inside the nanoparticle "incubator" to then create free radicals outside the nanoparticle; and the subsequent use of the free radicals to kill adjacent malignant cancer cells, or treat other diseases or sun damage conditions on the skin covered by the particles. The use of the invention is not limited to skin, but would be effective on any body-lining surfaces such esophagus or intestinal tract.

These and other objects and advantages of the present invention, along with features of novelty appurtenant thereto, will appear or become apparent by reviewing the following detailed description of the invention.

BRIEF DESCRIPTION OF THE SEVERAL VIEWS OF THE DRAWINGS

In the following drawings, which form a part of the specification and which are to be construed in conjunction

FIG. 2 is a non-scale schematic view of a nanoparticle treatment method on skin with a blocking element.

DETAILED DESCRIPTION OF THE INVENTION

Figure 1:
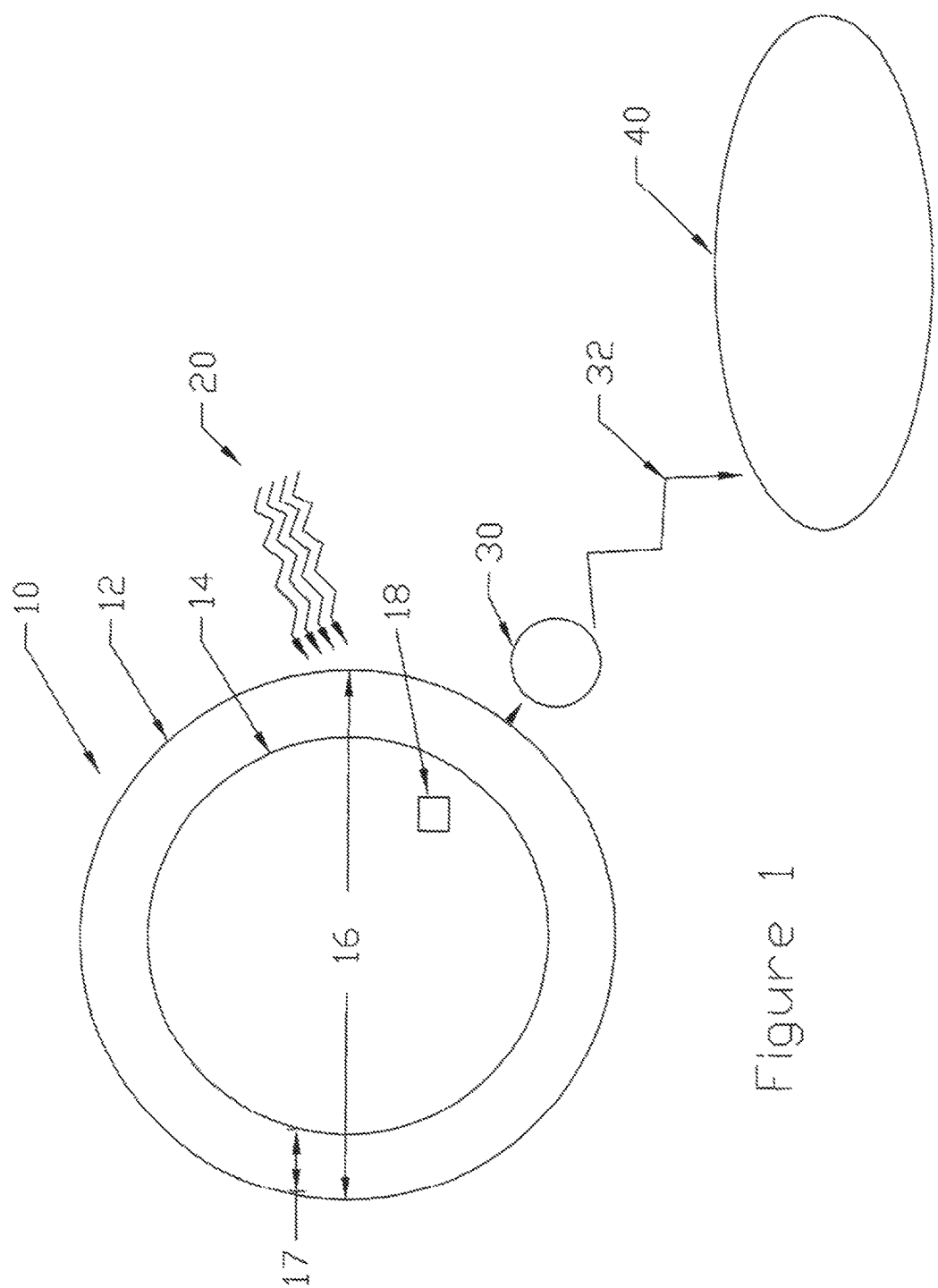
FIG. 1 is a non-scale schematic view of a nanoparticle based singlet oxygen generation.

As shown in FIG. 1 of the drawings, one exemplary embodiment of the present invention is generally shown based on a quantum active nanoparticle 10. The nanoparticle 10 has a silicon core 14 with a nanodimensial cross section 16 covered by an oxide and/or nitride outer shell 12 with a shell thickness 17. Note that the nanoparticle 10 is an individual nanoparticle 10 that is a discrete from other nanoparticles 10 such that each nanoparticle stands by itself such that it can be placed directly against the cancerous region of an individual. The nanoparticle 10 absorbs light energy 20 to form an exciton 18 to transfer the light energy to an adjacent oxygen molecule 30 to form singlet oxygen 32 for contacting a target cell 40 for initiating cell apoptosis. Note that here we are showing an individual nanoparticle and not silicon shell trapped in a colloid. A large scale colloid would block the light and keep the singlet oxygen 32 from contacting the cancer cell. Thus, the present invention teaches how to use colloid-free discrete core-shell nanoparticles 10 to allow for light to reach the cancer cell area to form the singlet oxygen 32 adjacent to the cancer cell.

The nanoparticle 10 is a silicon nanocrystal (Si—NC) encapsulated into $SiO_2$ (silicon oxide), $Si_3N_4$ (silicon nitrides) or $SiO_xN_y$ shell. These encapsulated nanoparticles 10 are quantum/optico active, inert chemically, yet still a biologically compatible material for UV radiation trapping processes based on band gap or quantum size effect of the Si—NC kernel. Average particles sizes for the entire nanoparticle that have proven viable are in the range from 2 to 5 nm. The shell of the nanoparticle is 0.5 to 1.5 nm thick and is included in the average size such that the core of the nanoparticle is 0.5 to 3.5 nm across. The size and density of the present encapsulated nanoparticles 10 can be adjusted to optimize the optical properties and the effectiveness of using these particles as singlet oxygen 32 photo-sensibilizers.

These silicon nanocrystals may be synthesized by known techniques including plasma formation, electro-chemical techniques or CO2—laser decomposition of monosilane SiH4 in an argon atmosphere. The specific nanoparticle crystals described herein for exciton formation were created by using high-quality/high purity silicon material and subjecting it in a controlled environment with resultant oxide, oxinitride, or nitride shell formation. The individual or specific shell 12, which covers the inner "core" 14 or silicon kernel of the nanocomposite, makes the material adequately inert and prevents it from further oxidation and degradation of its optical properties even at high temperatures up to 1073K. This also keeps them in individual form which is exceptionally useful for controlled application where large colloids would clog applicators or actually block the activation beam from reaching the targeted cells. In these initial runs, a preliminary chemical modification of the nanoparticles was done to cause a chemical thinning of the oxide shell. This was achieved by the treatment of the silicon dioxide shell of the composite material in an alkaline solution. This was necessary because the original nanoparticles were formed with composite oxide shells with up to a 2-10 nm thickness. This preliminary chemical modification was done to achieve an outer shell thickness in the 0.5-1.5 nm range for effective interaction with the oxygen molecules of the environmental air atmosphere.

As shown in FIG. 1, photo excitation of the encapsulated nanoparticle 10 results in exciton 18 formation within the nanoparticle 10. Photo excitation is preferably initiated by irradiating the nanoparticle 10 with visible light 20 of the Mercury lamp (Hg lamp DRSH500-2). Thus, excitation is done using light in the region of 350 to 600 nm or UV laser irradiation in the range of 300-400 nm. An example of laser irradiation would be N2-laser irradiation at ~340 nm. Once formed, an exciton 18 can then effectively transfer its energy to the oxygen molecules 30 adhered to the nanocrystal particle outer surface 12. The process of exciton formation also can effect the production of peroxide ions, $O_2$—. The singlet oxygen 32 production process is based on the close lying energies of excitons and the electronic transition energies of the oxygen molecules. As a result, the resonance charge transition process is realized in this transfer, also known as the so called Dexter process. A simple understanding of why this process is required is based on oxygen itself. The $O_2$ molecule in its ground state has spin equal 1 and, as a result, its state is triplet, $^3\Sigma$. The nearest excited states are singlet with the spin equal to zero (O), with the energies of 0.98 eV and 1.63 eV, $^1\Delta$ and $^1\Sigma$ respectively. Because direct excitation of the electronic states $^1\Delta$ and $^1\Sigma$ are spin forbidden, we need this nanocrystal 10 and the photo-sensibilization to generate the excited singlet states of an oxygen molecule 30.

As shown in FIG. 2 of the drawings, application of this photo-sensibilizing nanoparticle can be simplified by use of simple creams or gels 50. The individual nanoparticles 10 are each placed together to form a concentration quantity in a non-hydrophobic gel 50 or topical cream, lotion, or other topical medium but not in such great concentration that it block the ability of the light 20 to penetrate to form the singlet oxygen 32 in proximity to the cancerous cell. The non-hydrophobic characteristic is important to provide free oxygen for the formation of the singlet oxygen 32. The non-hydrophobic nanoparticle gel 50 can be applied directly onto the skin surface of abnormal or cancerous lesions 40 were the nanoparticle gel is then irradiated by the visible light 20 of the Mercury lamp 22, UV laser, halogen, or other appropriate source that generates the requisite wavelength. Exposure time, as well as radiation dosage must be correlated with clinical observations. Normal tissues 42 cells may be protected from the treatment process by covering with an opaque substance 60 that prevents exposure to the light source stimulus by blocking extra light 62. In this manner, the affected area can be controlled by both the area of application of the cream or gel, and the area exposed to the requisite light source. This provides for multiple protections for healthy tissue surrounding the problem area or tumor.

As an example of the process we detail the following exposure and death of cancer cells caused by the singlet oxygen 32 formed by the exposed nanoparticles and atmospheric oxygen that results in the death of the cancer cells. Melanoma cancer cells of the line 3T3 NIH (modified mouse fibroblasts) were grown by using standard procedure in vitro in a Petri dish. Nanoparticles were provided into the dish in close proximity to the cancer cells and atmospheric oxygen was also made available. After one hour exposure time to the Hg lamp radiation of an intensity of ~1 $mW/cm^2$@37° C. and fixed pH=7.2, 80% of the cancer cells exposed were stimulated and induced to natural cell death by the apoptosis mechanism.

This entire sequence of the treatment process is by visible light stimulation of inert nanoparticles. This differs from prior radiation cancer cell eradication techniques that have been accomplished by overexposure to chemicals, ingestion of chemicals into the body, and other mechanisms/processes based on ionizing radiation treatments or by photo stimulation of particles that cause cell death by necrosis/chemical means rather than by stimulation of the apoptosis mechanism. This is critical because the apoptosis mechanism is a non-inflammatory response that does not scar or damage surrounding tissue or cause dis-comfort to the patient. Furthermore, the light radiation wavelength and energies that are utilized do not require special handling or care techniques. Additionally, because the nanoparticles are inert, they are not a harmful substance that requires special handling or care. In this manner, a modified nanoparticle can be used for treating patients with diseases and conditions including, but not limited to, skin cancer, psoriasis, severe actinic conditions, retention keratosis and epidermal hypertrophic conditions, and other skin diseases or damage with a minimum of cost and complexity.

Reference numerals used throughout the detailed description and the drawings correspond to the following elements:

individual oxide/nitride silicon nanoparticle 10
outer shell 12
silicon core 14
nanodimensial cross section 16
shell thickness 17
light energy 20
lamp 22
exciton 18
oxygen molecule 30
target cell 40
normal tissues 42
gels 50
abnormal or cancerous lesions 40
opaque substance 60
blocked light 62

From the foregoing, it will be seen that this invention well adapted to obtain all the ends and objects herein set forth, together with other advantages which are inherent to the structure. It will also be understood that certain features and subcombinations are of utility and may be employed without reference to other features and subcombinations. This is contemplated by and is within the scope of the claims. Many possible embodiments may be made of the invention without departing from the scope thereof. Therefore, it is to be understood that all matter herein set forth or shown in the accompanying drawings is to be interpreted as illustrative and not in a limiting sense.

When interpreting the claims of this application, method claims may be recognized by the explicit use of the word 'method' in the preamble of the claims and the use of the 'ing' tense of the active word. Method claims should not be interpreted to have particular steps in a particular order unless the claim element specifically refers to a previous element, a previous action, or the result of a previous action. Apparatus claims may be recognized by the use of the word 'apparatus' in the preamble of the claim and should not be interpreted to have 'means plus function language' unless the word 'means' is specifically used in the claim element. The words 'defining,' 'having,' or 'including' should be interpreted as open ended claim language that allows additional elements or structures. Finally, where the claims recite "a" or "a first" element of the equivalent thereof, such claims should be understood to include incorporation of one or more such elements, neither requiring nor excluding two or more such elements.

What is claimed is:

1. A method for skin cancer treatment comprising:
    a) providing a medium comprising photo-sensibilizing nanoparticles, wherein the nanoparticles comprise
       a silicon core; and
       an individually discrete reactant outer shell having a thickness less than 1.5 nanometers, the silicon core and an individually discrete reactant outer shell, forming a colloid-free and individually discrete nanoparticle;
       the reactant outer shell formed from at least one shell reactant selected from the reactant group consisting of oxygen and nitrogen, and
       the combined silicon core and reactant outer shell having a cross section distance of greater than 2 and less than 9 nanometers;
    b) placing the medium comprising photo-sensibilizing nanoparticles provided in step (a) on the surface of skin cancer cells in a free oxygen environment;
    c) irradiating the medium covering the cancer cells with a laser or light beam in the visible spectrum of 320-650 nanometer wavelength;
    wherein exposure of the nanoparticle to the laser or light beam causes formation of singlet oxygen from the oxygen molecules adjacent the exterior surface of the nanoparticle, which results in the death of cancer cells.

2. The method of claim 1, wherein the medium is a paste, gel, or solution.

3. The method of claim 1, wherein the skin cancer is melanoma.

4. The method of claim 1, wherein the shell of the nanoparticle is 0.5 nm to 1.5 nm thick.

5. The method of claim 1, wherein the core of the nanoparticle is 0.5 nm to 3.5 nm across.

6. The method of claim 1, wherein the irradiation is performed with a $N_2$ laser at a wavelength of 340 nm.

7. The method of claim 1, wherein the medium is a topical cream.

* * * * *